United States Patent
Furuichi et al.

(10) Patent No.: US 9,572,496 B2
(45) Date of Patent: Feb. 21, 2017

(54) IMAGING APPARATUS FOR DIAGNOSIS, INFORMATION PROCESSING APPARATUS, CONTROL METHOD THEREOF, PROGRAM AND COMPUTER-READABLE STORAGE MEDIUM

(71) Applicant: TERUMO KABUSHIKI KAISHA, Shibuya-ku, Tokyo (JP)

(72) Inventors: Junya Furuichi, Hadano (JP); Kouichi Inoue, Odawara (JP); Hijiri Etou, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 16 days.

(21) Appl. No.: 14/806,119

(22) Filed: Jul. 22, 2015

(65) Prior Publication Data

US 2015/0320317 A1 Nov. 12, 2015

Related U.S. Application Data

(63) Continuation of application No. PCT/JP2013/000327, filed on Jan. 23, 2013.

(51) Int. Cl.
- *G06K 9/00* (2006.01)
- *A61B 5/00* (2006.01)
- *G06T 11/00* (2006.01)
- *G06T 7/00* (2006.01)
- *A61B 5/02* (2006.01)

(Continued)

(52) U.S. Cl.
CPC ........ *A61B 5/0066* (2013.01); *A61B 1/00009* (2013.01); *A61B 5/0084* (2013.01); *A61B 5/02007* (2013.01); *A61B 5/6852* (2013.01); *A61B 5/742* (2013.01); *G06T 7/0002* (2013.01); *G06T 11/003* (2013.01); *A61B 2576/02* (2013.01); *G06T 2207/10072* (2013.01); *G06T 2207/30101* (2013.01); *G06T 2211/40* (2013.01)

(58) Field of Classification Search
CPC .............. G06K 9/00; G06T 11/00; A61B 5/00
USPC .... 382/128, 129, 130, 131; 378/4, 8, 21–27; 600/407, 410, 411, 425
See application file for complete search history.

(56) References Cited

U.S. PATENT DOCUMENTS

| | | | |
|---|---|---|---|
| 8,040,524 B2 * | 10/2011 | Ozawa | A61B 5/0066 356/479 |
| 9,084,562 B2 * | 7/2015 | Kakuma | A61B 3/102 |

(Continued)

FOREIGN PATENT DOCUMENTS

JP  2007-267867 A  10/2007

OTHER PUBLICATIONS

June 15, 2016 extended European Search Report issued in corresponding European Application No. 13873103.9.

*Primary Examiner* — Abolfazl Tabatabai
(74) *Attorney, Agent, or Firm* — Buchanan Ingersoll & Rooney PC

(57) ABSTRACT

An imaging apparatus for diagnosis and a control method of an imaging apparatus for diagnosis are disclosed, which acquire line data represented by multiple luminance values in a radial direction from a rotation center position of an imaging core, which are derived by a rotation position and movement of the imaging core. Then, based on the acquired line data, an image of a two-dimensional space in which θ representing a rotation angle and z representing a position in a movement direction are set to two axes is generated and displayed.

16 Claims, 11 Drawing Sheets

(51) Int. Cl.
*A61B 1/00* (2006.01)
*A61B 6/00* (2006.01)
*A61B 5/05* (2006.01)

(56) References Cited

U.S. PATENT DOCUMENTS

2007/0232891 A1 10/2007 Hirota
2010/0094127 A1 4/2010 Xu
2012/0075638 A1 3/2012 Rollins et al.

* cited by examiner

IMAGING APPARATUS FOR DIAGNOSIS, INFORMATION PROCESSING APPARATUS, CONTROL METHOD THEREOF, PROGRAM AND COMPUTER-READABLE STORAGE MEDIUM

RELATED APPLICATION(S)

This application is a continuation of International Application No. PCT/JP2013/000327 filed on Jan. 23, 2013, the entire content of which is incorporated herein by reference.

FIELD

The present disclosure relates to a technique for generating a tomographic image of biological tissues by using light.

BACKGROUND INFORMATION

Intravascular treatment has been carried out by using a highly functional catheter such as a balloon catheter, a stent, or the like. An imaging apparatus for diagnosis such as an optical coherence tomography (OCT) apparatus has been generally used in order to perform preoperative diagnosis or to check postoperative progress.

The optical coherence tomography apparatus includes a built-in optical fiber, to a distal end of which an imaging core having an optical lens and an optical mirror is attached. At least a distal end portion of the optical fiber has a transparent sheath. Then, the sheath is inserted into a blood vessel of a patient. While the imaging core is rotated, light is emitted to an intravascular wall via the optical mirror. The reflection light from the blood vessel is received again via the optical mirror, and radial scanning is performed, thereby configuring a cross-sectional image of the blood vessel, based on the obtained reflection light. Then, while the optical fiber is rotated, a pulling operation (generally called pull-back) is performed at a predetermined speed, thereby forming a three-dimensional image of an inner wall in the longitudinal direction of the blood vessel (refer to JP-A-2007-267867). In addition, as an improved OCT type, a swept-source optical coherence tomography (SS-OCT) apparatus utilizing wavelength sweeping has also been developed.

An important point in examining the postoperative progress after the stent indwells the blood vessel can be to check how closely a vascular lumen surface is in contact (familiar) with the stent. However, when the three-dimensional image is used to display the postoperative progress, a diagnostician has to check the three-dimensional image by setting various viewpoint positions, thereby causing a relatively complicated operation. In addition, whenever the viewpoint position is changed, the diagnostician has to perform a calculation for generating the three-dimensional image, which can be observed from the changed viewpoint position. Consequently, a high-level response to a user's operation cannot be expected.

SUMMARY

A technique is disclosed, which can enable a user to easily check postoperative progress without a need to perform a complicated operation after a stent indwells.

An imaging apparatus is disclosed for diagnosis which reconfigures a three-dimensional image of a blood vessel by using a probe emitting light toward a vascular lumen surface and accommodating an imaging core for detecting reflection light from the blood vessel, to move the imaging core along the probe at a predetermined speed while the imaging core is rotated. The apparatus can include deriving means for deriving line data configured to include multiple luminance values arrayed side by side in a radial direction from the rotation center of the imaging core per each rotation angle in the rotation, based on data obtained by the imaging core during a period while the imaging core is rotated and moved, calculation means for calculating two-dimensional image data in which θ, z are set to two axes, by calculating a representative pixel value P (θ, z) in a viewing direction toward the radial direction from the rotation center of the imaging core in each line data L (θ, z), when the rotation angle of the imaging core is defined as θ and the line data at a movement position z in the movement is defined as L (θ, z), and display means for displaying the calculated two-dimensional image data.

A control method of an imaging apparatus is disclosed for diagnosis in which a three-dimensional image of a blood vessel is reconfigured by using a probe emitting light toward a vascular lumen surface and accommodating an imaging core for detecting reflection light from the blood vessel, and to move the imaging core along the probe at a predetermined speed while the imaging core is rotated, the method comprising: deriving line data configured to include multiple luminance values arrayed side by side in a radial direction from a rotation center of the imaging core per each rotation angle in a rotation, based on data obtained by the imaging core during a period while the imaging core is rotated and moved; calculating two-dimensional image data in which θ, z are set to two axes, by calculating a representative pixel value P (θ, z) in a viewing direction toward the radial direction from the rotation center of the imaging core in each line data L (θ, z), where the rotation angle of the imaging core is defined as θ and the line data at a movement position z in the movement is defined as L (θ, z); and displaying the calculated two-dimensional image data.

An information processing apparatus is disclosed that generates a three-dimensional image, based on data transmitted from an imaging core obtained from an imaging apparatus for diagnosis which reconfigures the three-dimensional image of a blood vessel by using a probe emitting light toward a vascular lumen surface and accommodating an imaging core for detecting reflection light from the blood vessel, and to move the imaging core along the probe at a predetermined speed while the imaging core is rotated, the information processing apparatus comprising: deriving means for deriving line data configured to include multiple luminance values arrayed side by side in a radial direction from a rotation center of the imaging core per each rotation angle in a rotation, based on data obtained by the imaging core during a period while the imaging core is rotated and moved; calculation means for calculating two-dimensional image data in which θ, z are set to two axes, by calculating a representative pixel value P (θ, z) in a viewing direction toward the radial direction from the rotation center of the imaging core in each line data L (θ, z), when the rotation angle of the imaging core is defined as θ and the line data at a movement position z in the movement is defined as L (θ, z); and display means for displaying the calculated two-dimensional image data.

A control method of an information processing apparatus is disclosed that generates a three-dimensional image, based on data transmitted from an imaging core obtained from an imaging apparatus for diagnosis which reconfigures the three-dimensional image of a blood vessel by using a probe emitting light toward a vascular lumen surface and accommodating an imaging core for detecting reflection light from the blood vessel, and to move the imaging core along the probe at a predetermined speed while the imaging core is rotated, the method comprising: deriving line data configured to include multiple luminance values arrayed side by side in a radial direction from a rotation center of the imaging core per each rotation angle in a rotation, based on data obtained by the imaging core during a period while the imaging core is rotated and moved; calculating two-dimensional image data in which θ, z are set to two axes, by calculating a representative pixel value P (θ, z) in a viewing direction toward the radial direction from the rotation center of the imaging core in each line data L (θ, z), when the rotation angle of the imaging core is defined as θ and the line data at a movement position z in the movement is defined as L (8, z); and displaying the calculated two-dimensional image data.

A non-transitory computer-readable recording medium is disclosed with a program stored therein which causes a computer to execute a control method of an information processing apparatus that generates a three-dimensional image, based on data transmitted from an imaging core obtained from an imaging apparatus for diagnosis which reconfigures the three-dimensional image of a blood vessel by using a probe emitting light toward a vascular lumen surface and accommodating an imaging core for detecting reflection light from the blood vessel, and to move the imaging core along the probe at a predetermined speed while the imaging core is rotated, the method comprising: deriving line data configured to include multiple luminance values arrayed side by side in a radial direction from a rotation center of the imaging core per each rotation angle in a rotation, based on data obtained by the imaging core during a period while the imaging core is rotated and moved; calculating two-dimensional image data in which θ, z are set to two axes, by calculating a representative pixel value P (θ, z) in a viewing direction toward the radial direction from the rotation center of the imaging core in each line data L (θ, z), when the rotation angle of the imaging core is defined as θ and the line data at a movement position z in the movement is defined as L (θ, z); and displaying the calculated two-dimensional image data.

BRIEF DESCRIPTION OF THE DRAWINGS

The accompanying drawings are incorporated in the description, configure a part of the description, represent embodiments of the present disclosure, and are used to describe principles of the present disclosure together with the description.

DETAILED DESCRIPTION

According to the present description, postoperative progress can be relatively easily checked without a need to perform a complicated operation after a stent indwells.

Hereinafter, an embodiment according to the present disclosure will be described in detail with reference to the accompanying drawings.

Figure 1:
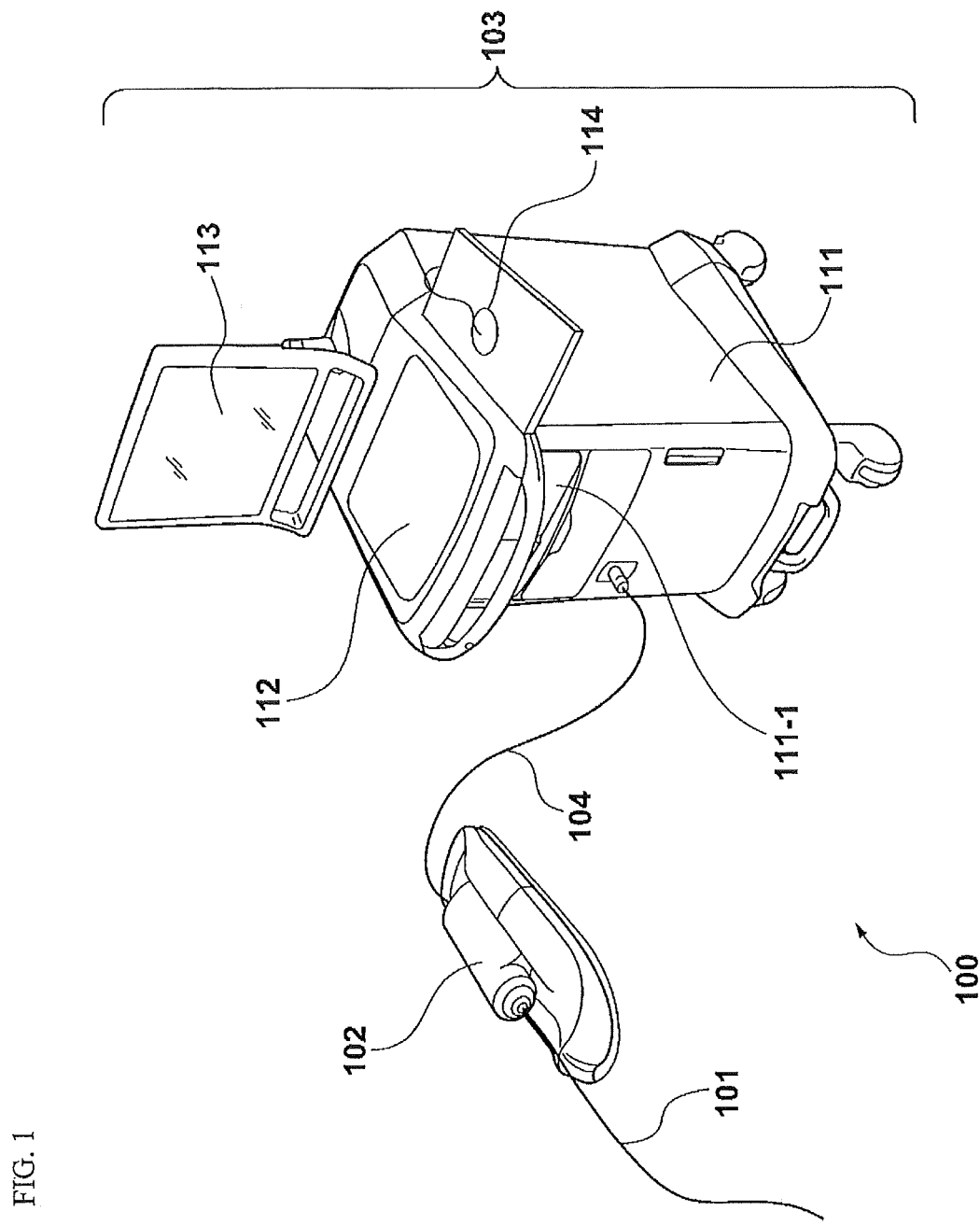
FIG. 1 is a view illustrating an external configuration of an imaging apparatus for diagnosis according to an exemplary embodiment.

FIG. 1 is a view illustrating an external configuration of an imaging apparatus for diagnosis 100 according to an embodiment of the present disclosure.

As illustrated in FIG. 1, the imaging apparatus for diagnosis 100 can includes a probe unit 101, a scanner and pull-back unit 102, and an operation control device 103. The scanner and pull-back unit 102 and the operation control device 103 can be connected to each other by a signal line 104 so that various signals can be transmitted.

The probe unit 101 has an internally inserted imaging core which is directly inserted into a blood vessel and includes an optical transceiver which continuously transmits transmitted light (measurement light) into the blood vessel and which continuously receives reflected light from the inside of the blood vessel. The imaging apparatus for diagnosis 100 measures an intravascular state by using the imaging core.

The probe unit 101 is detachably attached to the scanner and pull-back unit 102. A motor incorporated in the scanner and pull-back unit 102 is driven, thereby regulating an intravascular operation in the axial direction and an intravascular operation in the rotation direction of the imaging core, which is internally inserted into the probe unit 101.

The operation control device 103 can include a function for inputting various setting values upon each measurement, and a function for processing data obtained by the measurement and for displaying various blood vessel images.

In the operation control device 103, the reference numeral 111 represents a main body control unit. The main body control unit 111 generates interference light data by causing reflected light obtained by the measurement to interfere with reference light obtained by separating the light from a light source, and generates an optical cross-sectional image by processing line data generated based on the interference light data.

The reference numeral 111-1 represents a printer and DVD recorder, which prints a processing result in the main body control unit 111 or stores the processing result as data. The reference numeral 112 represents an operation panel, and a user inputs various setting values and instructions via the operation panel 112. The reference numeral 113 represents an LCD monitor as a display device, which displays a cross-sectional image generated in the main body control unit 111. The reference numeral 114 represents a mouse serving as a pointing device (coordinate input device).

Figure 2:
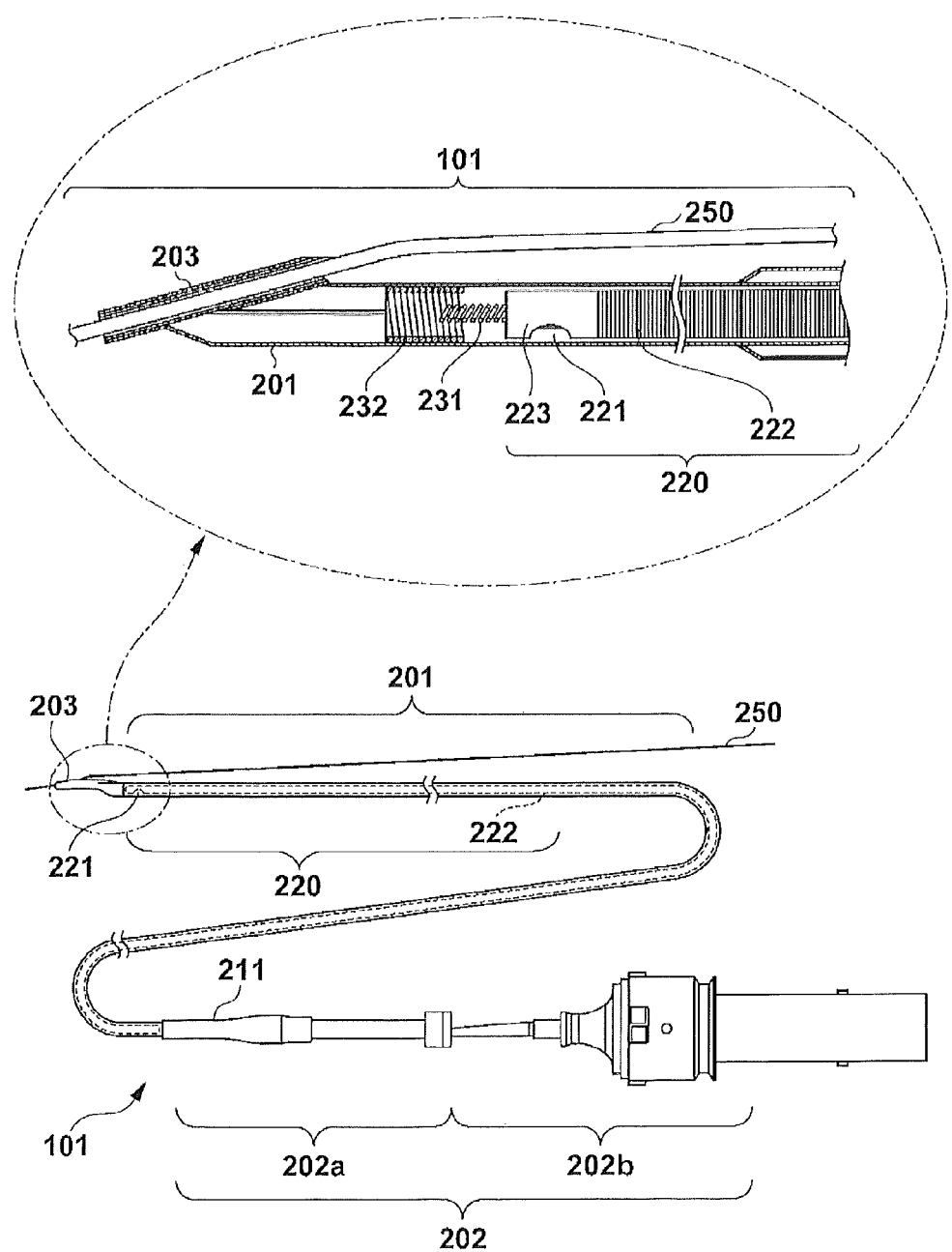
FIG. 2 is a view illustrating an overall configuration of a probe unit and a cross-sectional configuration of a distal end portion.

Next, an overall configuration of the probe unit 101 and a cross-sectional configuration of a distal end portion will be described with reference to FIG. 2. As illustrated in FIG. 2, the probe unit 101 is configured to include a long catheter sheath 201 to be inserted into the blood vessel and a connector unit 202 to be arranged on the front side of a user so as to be operated by the user without being inserted into the blood vessel. A guidewire lumen tube 203, which can fix a guidewire 250 for guiding the probe unit 101 to a position of a diagnosis-targeted blood vessel is disposed in the distal end of the catheter sheath 201. The catheter sheath 201 has a lumen, which is continuously formed from a connection portion with the guidewire lumen tube 203 to a connection portion with the connector unit 202.

An imaging core 220 which internally can include a transceiver 221 in which the optical transceiver for transmitting and receiving the light is arranged and which can include a coil-shaped drive shaft 222 internally including an optical fiber cable and transmitting rotary drive power for rotating the transceiver 221 is inserted into the lumen of the catheter sheath 201 over substantially the entire length of the catheter sheath 201.

The connector unit 202 can include a sheath connector 202a configured to be integral with a proximal end of the catheter sheath 201, and a drive shaft connector 202b which is configured to rotatably fix the drive shaft 222 to the proximal end of the drive shaft 222.

An anti-kink protector 211 is disposed in a boundary section between the sheath connector 202a and the catheter sheath 201. The anti-kink protector 211 can help maintain predetermined rigidity, and can help prevent bending (kink) caused by a rapid change in physical properties.

The proximal end of the drive shaft connector 202b is detachably attached to the scanner and pull-back unit 102.

A housing 223 can have a shape in which a short cylindrical metal pipe partially has a cutout portion, and is formed by being cut out from a metal ingot, or is molded metal powder injection molding (MIM). In addition, an elastic member 231 having a short coil shape can be disposed on the distal end side.

The elastic member 231 can be obtained by forming a stainless steel wire into a coil shape. The elastic member 231 is arranged on the distal end side, thereby helping prevent the imaging core 220 from being caught on the inside of the catheter sheath 201 when the imaging core 220 is moved forward and rearward.

The reference numeral 232 represents a reinforcement coil, which is disposed in order to prevent rapid bending of the distal end portion of the catheter sheath 201.

The guidewire lumen tube 203 has a guidewire lumen into which a guidewire 250 can be inserted. The guidewire 250 is used in guiding the distal end of the catheter sheath 201b to a lesion.

Figure 3:
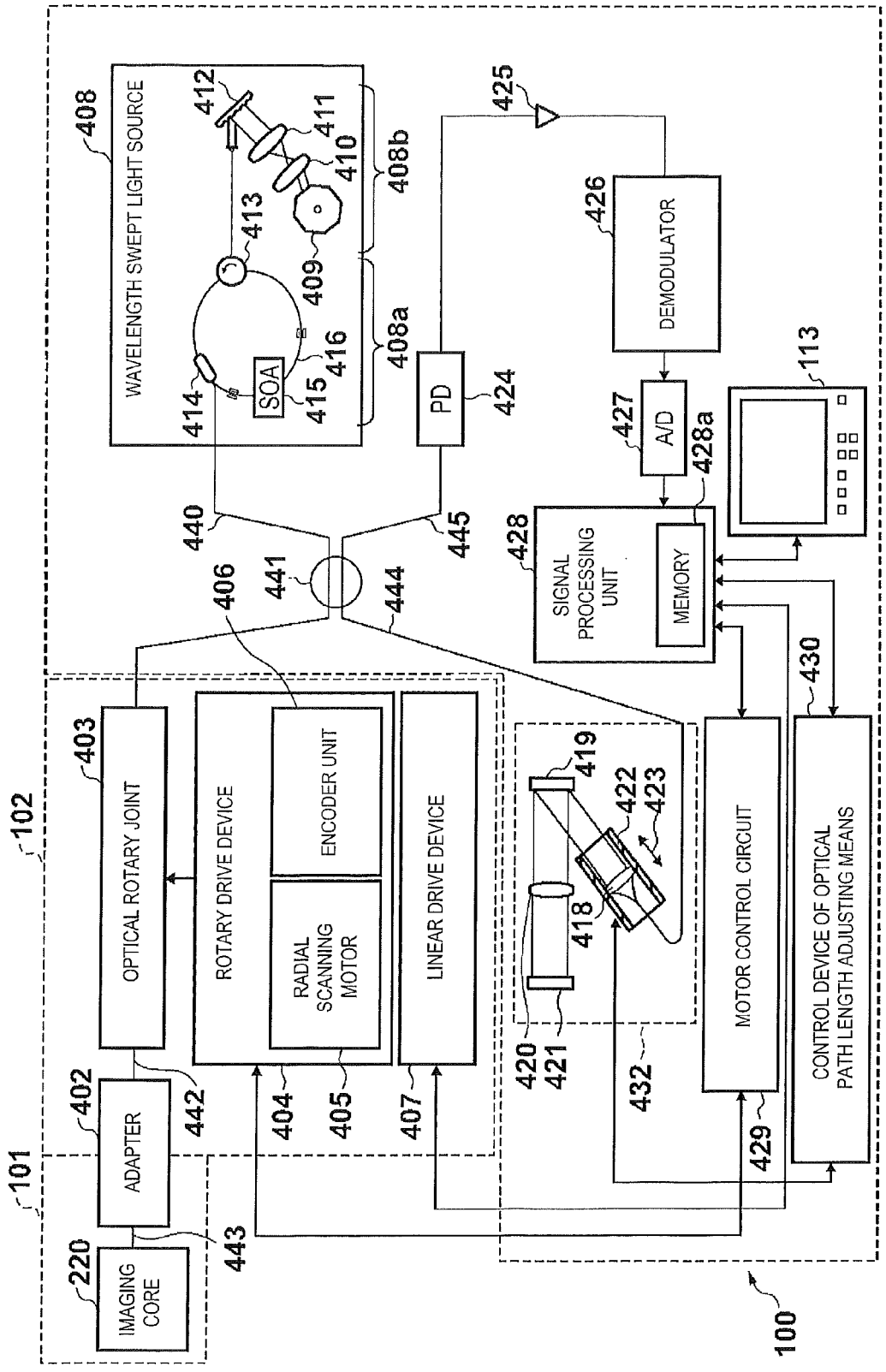
FIG. 3 is a diagram illustrating a functional configuration of the imaging apparatus for diagnosis.

Next, a functional configuration of the imaging apparatus for diagnosis 100 will be described. FIG. 3 is a diagram illustrating the functional configuration of the imaging apparatus for diagnosis 100 which can include an OCT function (here, a swept source OCT as an example). Hereinafter, the functional configuration of the swept source OCT will be described with reference to the same drawings.

In the drawing, the reference numeral 408 represents a wavelength swept light source (swept laser), and is one type of an extended-cavity laser which can include an optical fiber 416 which is coupled to a semiconductor optical amplifier (SOA) 415 in a ring shape and a polygon scanning filter (408b).

Light output from the SOA 415 proceeds to the optical fiber 416, and enters the polygon scanning filter 408b. The light whose wavelength is selected here is amplified by the SOA 415, and is finally output from a coupler 414.

The polygon scanning filter 408b selects the wavelength in combination with a diffraction grating 412 for diffracting the light and a polygon mirror 409. For example, the light diffracted by the diffraction grating 412 can be concentrated on a surface of the polygon mirror 409 by two lenses (410 and 411). In this manner, only the light having a wavelength orthogonal to the polygon mirror 409 returns through the same optical path, and is output from the polygon scanning filter 408b. For example, time sweeping of the wavelength can be performed by rotating the polygon mirror 409.

For example, a 32-sided mirror can be used for the polygon mirror 409 whose rotation speed is approximately 50000 rpm. A wavelength swept system in which the polygon mirror 409 and the diffraction grating 412 are combined with each other can help enable high speed and high output wavelength sweeping.

The light of a wavelength swept light source 408 which is output from the coupler 414 is incident on one end of a first single mode fiber 440, and is transmitted to the distal end side. The first single mode fiber 440 is optically coupled to a second single mode fiber 445 and a third single mode fiber 444 in an optical coupler 441. The optical coupler 441 can be located between the first single mode fiber 440 and the second 442 and third single mode fiber 444.

On the further distal end side than the optical coupler 441 of the first single mode fiber 440, an optical rotary joint (optical coupling unit) 403 which transmits the light by coupling a non-rotating part (fixed portion) and a rotating part (rotary drive unit) to each other is disposed inside the rotary drive device 404.

Furthermore, a fifth single mode fiber 443 of the probe unit 101 can be detachably connected via the adapter 402 to the distal end side of a fourth single mode fiber 442 inside the optical rotary joint (optical coupling unit) 403. In this manner, the light from the wavelength swept light source 408 is transmitted to the fifth single mode fiber 443 which is inserted into the imaging core 220 and can be rotatably driven.

In accordance with an exemplary embodiment, the transmitted light can be emitted from the optical transceiver 221 of the imaging core 220 to the biological tissues inside the blood vessel while a rotary operation and an axial operation are performed. Then, the reflected light scattered on a surface or inside the biological tissues can be partially captured by the optical transceiver 320 of the imaging core 220, and returns to the first single mode fiber 440 side through a rearward optical path. Furthermore, the light can be partially transferred to the second single mode fiber 445 side by the optical coupler 441, and can be emitted from one end of the second single mode fiber 445. Thereafter, the light can be received by an optical detector (for example, a photodiode 424).

The rotary drive unit side of the optical rotary joint 403 is rotatably driven by the radial scanning motor 405 of the rotary drive device 404.

In accordance with an exemplary embodiment, an optical path length variable mechanism 432 for finely adjusting an optical path length of reference light is disposed in the distal end opposite to the optical coupler 441 of the third single mode fiber 444.

In order for variations in the length of an individual probe unit 101 to be absorbed when the probe unit 101 is replaced and newly used, this optical path length variable mechanism 432 can include optical path length changing means for changing an optical path length corresponding to the variations in the length.

The third single mode fiber 444 and a collimating lens 418 are disposed on a one-axis stage 422 which is movable in an optical axis direction of the one-axis stage 422 as illustrated by an arrow 423, thereby forming the optical path length changing means.

For example, the one-axis stage 422 can function as the optical path length changing means having a variable enough range of the optical path length to absorb the variations in the optical path length of the probe unit 101 when the probe unit 101 is replaced. Furthermore, the one-axis stage 422 can also include a function as adjusting means for adjusting an offset. For example, even when the distal end of the probe unit 101 is not in close contact with the surface of the biological tissues, the one-axis stage can finely change the optical path length. In this manner, the optical path length can be set in a state of interfering with the reflected light from the surface position of the biological tissues.

In accordance with an exemplary embodiment, the optical path length can be finely adjusted by the one-axis stage 422. The light reflected on a mirror 421 via a grating 419 and a lens 420 is mixed with the light obtained from the first single mode fiber 440 side by the optical coupler 441 disposed in the middle of the third single mode fiber 444, and then is received by the photodiode 424.

Interference light received by the photodiode 424 in this way is photoelectrically converted, and can be input to a demodulator 426 after being amplified by the amplifier 425. The demodulator 426 performs demodulation processing for extracting only a signal portion of the interference light, and an output from the demodulator 426 is input to the A/D converter 427 as an interference light signal.

The A/D converter 427 performs sampling on the interference light signal, for example, at 90 MHz by an amount of 2048 points, and generates digital data (interference light data) of one line. In accordance with an exemplary embodiment, the sampling frequency can be set to 90 MHz based on the assumption that approximately 90% of wavelength swept cycles (12.5 μsec) is extracted as the digital data of 2048 points, when a repetition frequency of the wavelength sweeping is set to 40 kHz. However, the sampling frequency is not particularly limited thereto.

The interference light data in the units of lines which is generated by the A/D converter 427 is input to the signal processing unit 428. The signal processing unit 428 generates data in a depth direction (line data) by performing frequency resolution on the interference light data using the fast Fourier transform (FFT), and the data is subjected to coordinate transformation. In this manner, an optical cross-sectional image is constructed at each intravascular position, and is output to the LCD monitor 113.

The signal processing unit 428 can be further connected to a control device of optical path length adjusting means 430. The signal processing unit 428 controls a position of the one-axis stage 422 via the control device of optical path length adjusting means 430.

The processing in the signal processing unit 428 can also be realized in such a way that a predetermined program causes a computer to execute the processing.

In the above-described configuration, if a user operates the operation control device 103 and inputs an instruction to start scanning, the signal processing unit 428 controls the scanner and pull-back unit 102 so as to rotate the imaging core 220 and pull the imaging core 220 at a predetermined speed so as to move in the longitudinal direction of the blood vessel. At this time, generally, a transparent flush solution can be caused to flow into the blood vessel until light emitting and light receiving performed by the imaging core 220 is prevented from being obstructed by the blood. Based on the above-described result, as described above, the A/D converter 427 comes to output the digital interference light data. Accordingly, the signal processing unit 428 can continuously build an optical cross-sectional image at each position along the movement direction of the imaging core 220, in a memory 428a belonging to the signal processing unit 428.

Figure 4:
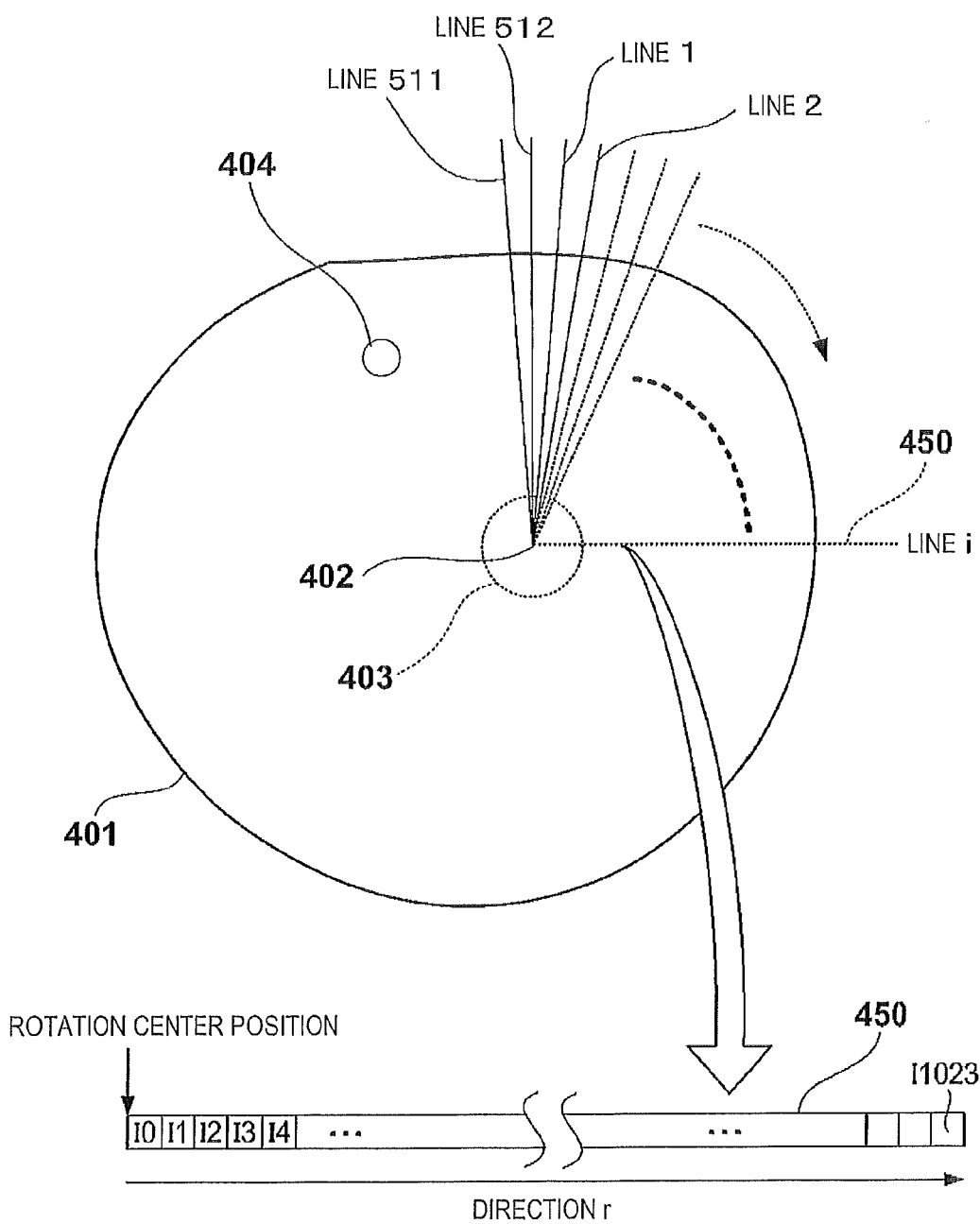
FIG. 4 is a view for illustrating reconfiguration processing of a cross-sectional image.

In accordance with an exemplary embodiment, processing for generating one sheet of the optical cross-sectional image will be described with reference to FIG. 4. FIG. 4 is a view for illustrating reconfiguration processing of the cross-sectional image of a blood vessel 401 in which the imaging core 220 is located. While the imaging core 220 is rotated once (rotation of 360 degrees), the measurement light is transmitted and received a plurality of times. The light transmitted and received once can obtain data of one line in a light-emitted direction. Accordingly, for example, during one rotation, 512 items of the line data radially extending from the rotation center 402 can be obtained by transmitting and receiving the light 512 times. The line data can be calculated by a known method, thereby continuously generating three-dimensional model data extending in the radial direction (direction r) from the rotation center position. For example, one line in this model data is configured to include 1024 luminance values l0 to l1023. The luminance value l0 represents the rotation center position, and the luminance value l1023 represents a luminance value at a position farthest from the rotation center position.

In the above-described manner, 512 items of line data can be continuously built. However, the items become closer to each other in the vicinity of the rotation center position, and become isolated from each other as the items are separated from the rotation center position. Accordingly, a pixel present in an empty space between the respective lines is continuously generated by performing known interpolation thereon so as to generate a cross-sectional image visible to humans. It should be noted that the center position of the cross-sectional image coincides with the rotation center position of the imaging core 220 and does not represent the center position of the blood vessel cross section.

When the light is transmitted and received, the light can also be reflected from the catheter sheath 201 itself. Accordingly, as illustrated in the drawing, a shadow 403 of the catheter sheath 201 can be formed on the cross-sectional image. In addition, the reference numeral 404 illustrated in the drawing is the shadow of the guidewire 250. In practice, the guidewire 250 is made of metal and the light is not transmitted therethrough. Thus, an image of a rear side portion of the guidewire 250 cannot be obtained when viewed from the rotation center position. The illustration is to be recognized as a merely conceptual diagram.

If a user operates the operation control device 103 and inputs an instruction to start scanning, the signal processing unit 428 controls the scanner and pull-back unit 102 so as to rotate the imaging core 220 and pull the imaging core 220 at a predetermined speed so as to move in the longitudinal direction of the blood vessel (pull-back processing). As a result, the signal processing unit 428 continuously builds multiple cross-sectional images taken along the pulling direction of the image core 220, in its own memory 428a.

Figure 5:
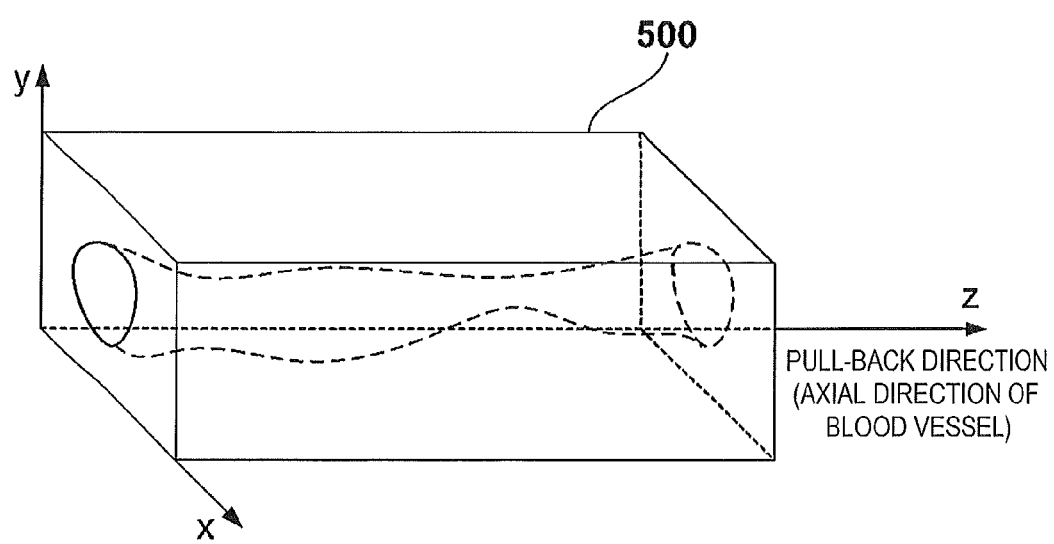
FIG. 5 is a view illustrating an example of three-dimensional model data of a blood vessel, which is reconfigured.

The reference numeral 500 in FIG. 5 illustrates a conceptual diagram of three-dimensional image data generated by connecting the multiple cross-sectional images built in the memory 428a to one another in the pull-back processing. The z axis illustrated in the drawing represents a pull-back direction (longitudinal direction of the blood vessel). As is known, if the thrombus or the like is present, a passage through which the blood flows is locally narrowed. A broken line illustrated in the drawing represents a boundary surface with the blood in the blood vessel. Hereinafter, the boundary surface is referred to as a vascular lumen surface. For example, it should be understood that the vascular lumen surface includes not only a blood vessel inner wall but also the thrombus.

In accordance with an exemplary embodiment, a case may be considered where the stent is arranged. In this case, the three-dimensional image as illustrated in FIG. 5 can be obtained. However, it is necessary to set various viewpoint positions in order to recognize which portion of the stent has a gap with the vascular lumen surface, and which portion is in contact with the vascular lumen surface. However, this can cause the operation to be complicated. Above all, processing for reconfiguring the three-dimensional image can use a large amount of calculations. Accordingly, it can be impractical to perform the reconfiguration processing of the three-dimensional image each time in response to a user's instruction to change the viewpoint position. Consequently, a high-level response to the user's operation cannot be expected.

In the present exemplary embodiment, instead of displaying a positional relationship between the stent and the vascular lumen surface as a three-dimensional image, the positional relationship is displayed as a two-dimensional image which does not require a change in the viewpoint position. Hereinafter, a principle thereof will be described with reference to FIGS. 6 to 9.

As described above, when the positional relationship between the stent and the vascular lumen surface is observed, a point which a user wants to recognize many is which portion of the stent has a gap with the vascular lumen surface, and which portion is in contact with the vascular lumen surface. In the present embodiment, the two-dimensional image, which can help enable the user to easily recognize the related point is generated. In addition, if the stent becomes familiar with the vascular lumen surface to some extent, even the lumen surface of the stent can be covered with vascular tissues. Therefore, the two-dimensional image according to the present embodiment can also help enable the user to easily observe the related point.

One line data 450 illustrated in FIG. 4 can be specified by a position in the longitudinal direction (z axis) of the blood vessel and a rotation angle θ. Then, one of 1024 luminance values in the line data 450 can be specified by a distance r (r is any one of 0, 1, 2, to 1023) from the rotation center position. Accordingly, it can be understood that any optional pixel value in the line data obtained by the pull-back processing can be specified in the space having three axes $\{z, \theta, \text{and } r\}$.

Figure 6:
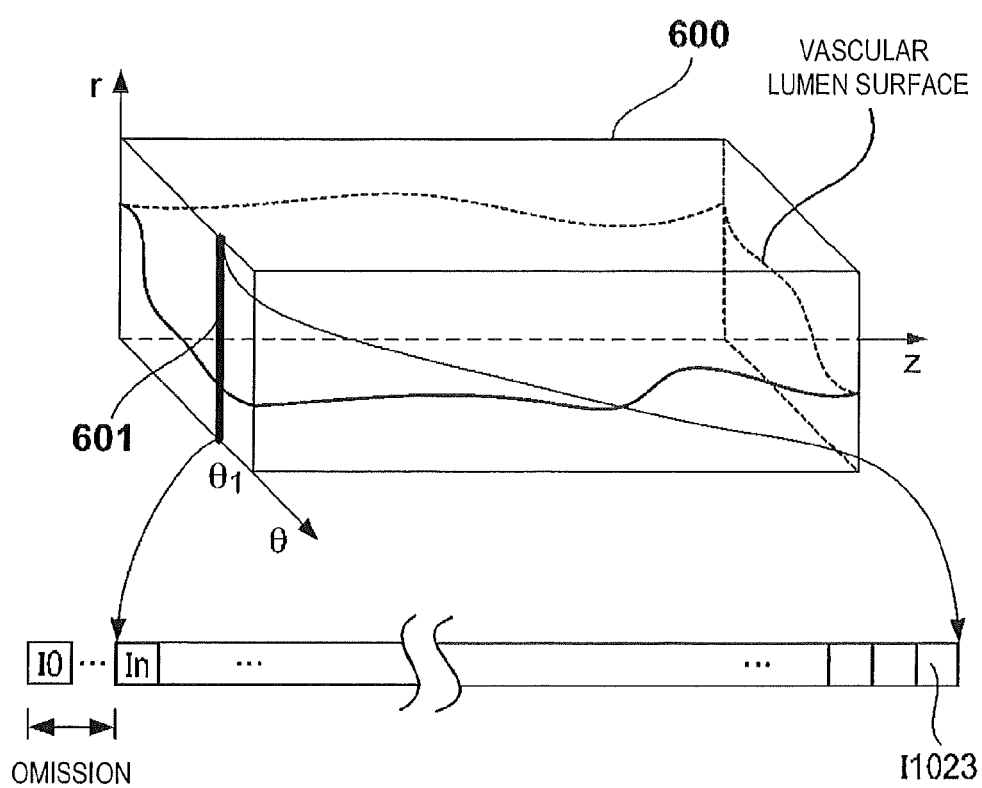
FIG. 6 is a view for illustrating an example of volume data when a two-dimensional image is generated according to the embodiment.

FIG. 6 illustrates a three-dimensional space defined by the three axes z, θ, and r. The reference numeral 601 illustrated in the drawing indicates the line data specified by an angle $\theta_1$ in a cross section of z=0. However, as described with reference to FIG. 4, data $l_0$ to $l_{n-1}$ (reference numeral 403 in FIG. 4) from the rotation center position to the surface of the catheter sheath 220 in one line data is data having no relationship with the blood vessel. Accordingly, the corresponding portion is cut away so as to handle the remaining luminance $l_n$ to $l_{1023}$ as valid data. In the three-dimensional space in FIG. 6, as a position has a smaller value of r, it is illustrated that the position is closer to the rotation center. The reference numeral n illustrated here represents a known value including an outer diameter of the catheter sheath 201.

In the present exemplary embodiment, the "two-dimensional image" obtained when a direction having a positive value of r is viewed from a position having a negative value of r is rebuilt in the three-dimensional space in FIG. 6. In short, the two-dimensional image of [θ-z] obtained when viewed from the rotation center position is reconfigured. The two-dimensional image is an image shown in a coordinate space between θ and z. Accordingly, a pixel value in the two-dimensional image can be expressed by P (z,θ). Therefore, hereinafter, a calculation method of the pixel value P (z,θ) will be described.

Figure 7:
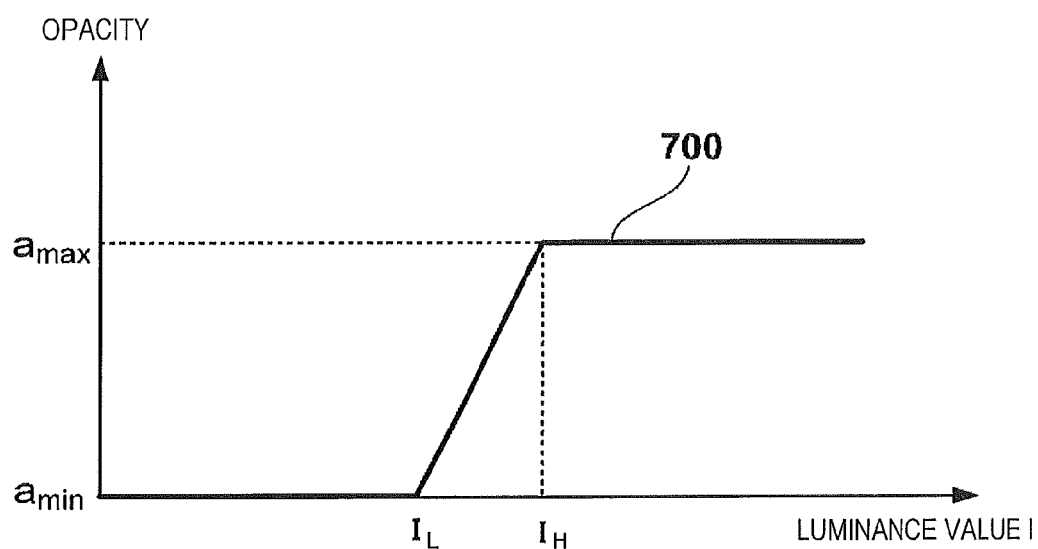
FIG. 7 is a view illustrating an example of an opacity conversion curve.

In the present exemplary embodiment, as illustrated in FIG. 7, each luminance value $l_m$ (m is any one of n to 1023) is converted into opacity by setting a conversion curve f which is shown by the luminance value and the opacity and is represented by the reference numeral 700. In the conversion curve f, when the luminance value is equal to or smaller than $l_L$, the opacity has the minimum value $a_{mm}$ (in the embodiment, $a_{min}$=0), for example, the transparency is maximized. In contrast, when the luminance value is equal to or greater than $l_H$, the opacity has the maximum value $a_{max}$, for example, the transparency is minimized. Then, a portion between the luminance values $l_L$ and $l_H$ has a linear shape. A user can freely move the conversion curve 700 in parallel along the z axis, and the meaning will be described later. By default, the opacity of the surface tissues on the vascular lumen surface which is obtained statistically can be set to have a value greater than the minimum value $a_{min}$.

In the present embodiment, in a relationship with a preset threshold value Th (in the embodiment, threshold value Th=1), the minimum value m satisfying the following equation is obtained.

$$f(l_n)+f(l_{n+1})+\ldots f(l_m)\geq Th$$

Then, the minimum value m is utilized, and a representative pixel value P (z, θ) representing the targeted line data is calculated by using the following equation:

$$P(z,\theta)=P_i=f(l_i)*I_i+(1-f(l_i))*P_{i-1}$$

When the representative pixel value of the targeted line data in the coordinates (θ, z) is calculated, instead of referring to the other line data, the representative pixel value is expressed as a function of only the position in the targeted line data as in the following equation:

$$P(z,\theta)=P_i=f(l_i)*I_i+(1-f(l_i))*P_{i-1}$$

Here, i is the index number of data points and rows in the direction r, and the relationship is expressed by n≤i≤m.

As described above, the above-described processing is to describe image generation of the "two-dimensional image" obtained when the direction having the positive value of r is viewed from the position having the negative value of r in the r axis in FIG. 6. However, without being limited to the related two-dimensional image, the viewpoint direction may be optionally rotated and moved in parallel by a user. When the viewpoint direction is rotated, the two-dimensional image to be displayed is displayed as a positive projection image in the viewing direction of the three-dimensional space illustrated in FIG. 6. As described above, in the processing content, a data group of {ln to lm} may be calculated by being replaced with a data group having the luminance values arrayed on the line of sight in FIG. 6. In this case, m can take a value greater than 1023.

The luminance value from the catheter sheath 201 to the vascular lumen surface is small due to an action of a flush solution. Therefore, the opacity therebetween is equal to or close to the minimum $a_{max}$ (maximum transparency). Then, if the stent reaches a surface of the vascular lumen surface, the opacity gradually increases along the depth direction. Accordingly, it can be described that the pixel value P (z, θ) represents a result of adding the opacity in the depth direction to some extent from the vascular lumen surface.

In contrast, for example, the stent is configured to have metal, and thus has a very high luminance (high reflection intensity). The high luminance representing the stent can have a sufficiently greater value as compared to the vascular tissues. Accordingly, it is convenient to distinguish the stent from the vascular lumen surface. The pixel value P (z, θ) obtained by the above-described calculation becomes a greater value as compared to the pixel value of the vascular lumen surface.

In addition, in a state where the stent is covered with the vascular tissues when viewed from the inner side of the stent, the opacity exceeding the minimum value $a_{min}$ of the vascular tissues is added to some extent in the above-described calculation process. Thereafter, the opacity representing the stent is added to the calculation process. The pixel value P (z, θ) obtained as a result becomes a much greater value as compared to that in a case where the stent is exposed. For example, a case where the stent is exposed on the blood flow surface and a case where the stent is covered with the vascular tissues can be discriminated from each other.

According to the two-dimensional image represented by the pixel P (z, θ) generated as described above, it is not possible to recognize whether the rear surface of the stent is in contact with the vascular lumen surface, or whether there is a gap from the rear surface to the vascular lumen surface. Therefore, interpolation processing can be performed on the two-dimensional image according to the present embodiment so that the related point can be discriminated.

In accordance with an exemplary embodiment, a principle of detecting a gap between the rear surface of the stent and the vascular lumen surface will be described with reference to FIG. 8.

The drawing is a perspective conceptual view when a blood vessel 800 is viewed from a position orthogonal to the longitudinal direction of the blood vessel 800. The reference numeral 850 illustrated in the drawing represents the stent. As previously described, the reference numeral 201 represents the catheter sheath, and the reference numeral 250 represents the guidewire.

Figure 8:
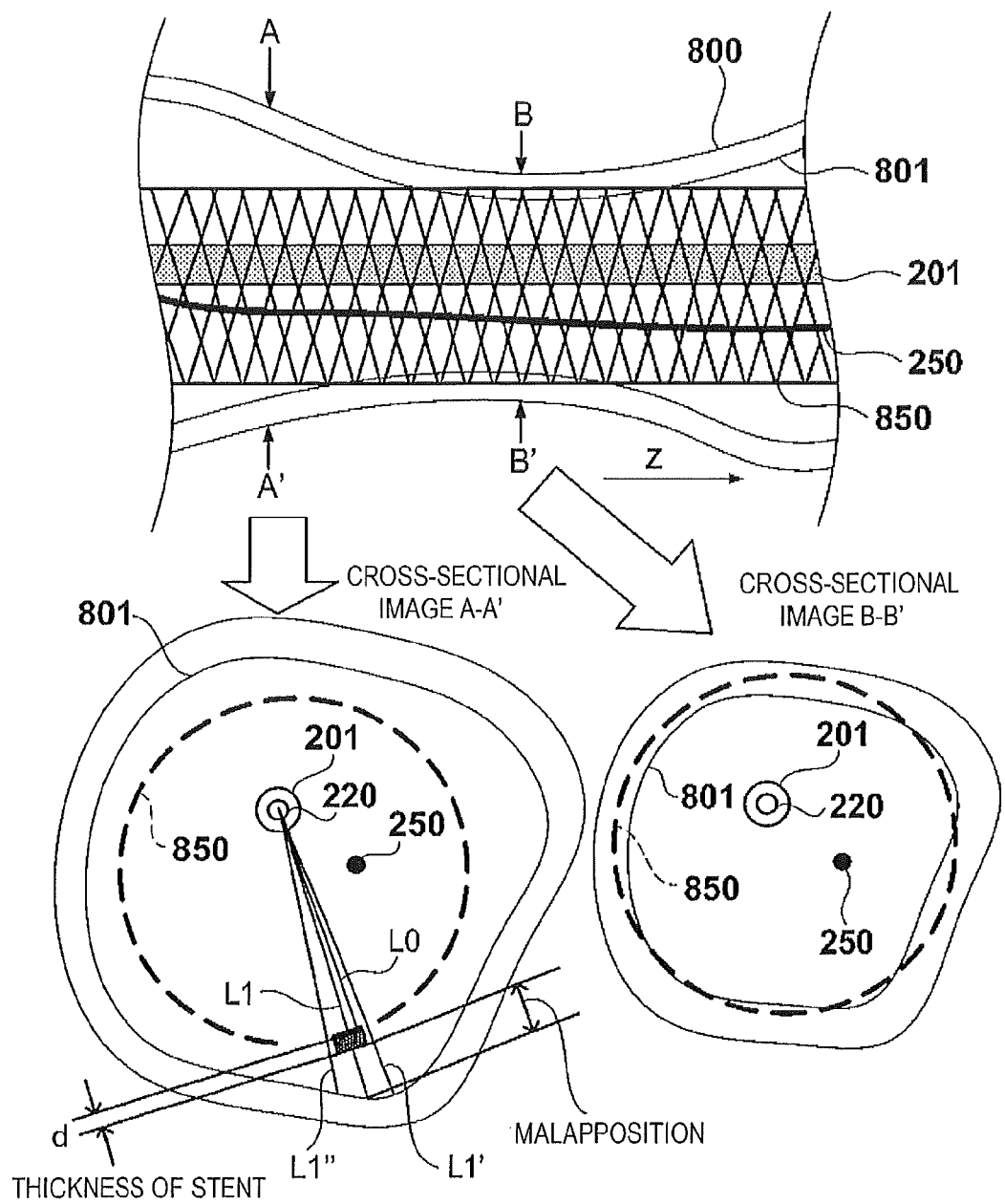
FIG. 8 is a view illustrating a relationship between a stent and a vascular lumen surface, and an example of a cross-sectional image orthogonal to a blood vessel axis.

The lower part of FIG. 8 illustrates respective cross-sectional views at a position A-A' and a position B-B' of the blood vessel 800.

In general, the stent 850 expands its diameter after indwelling a targeted vascular position. Thus, the stent 850 has a mesh structure. Accordingly, as illustrated in the cross-sectional view A-A' and the cross-sectional view B-B', the stent 850 is detected in a state of being scattered at discrete positions on the cross-sectional image obtained by one rotation viewed from the imaging core 220.

The cross-sectional image A-A' indicates that a gap is present over an entire angular range between the stent and a vascular lumen surface 801. In addition, the cross-sectional image B-B' indicates a state where a portion of the stent is covered with the vascular tissues. In addition, the stent 850 and the guidewire 250 are generally made of metal. Thus, the reflectivity of the light can be very high and thus the light is not transmitted therethrough. Accordingly, an image on the rear side of the stent 850 and the guidewire 250 cannot be obtained when viewed from the imaging core 220. It should be noted that the illustration is merely a conceptual view. Although details will be described later, a method of discriminating the guidewire and the stent from each other will be described later.

Based on the cross-sectional view, a distance L0 from the rotation center position of the imaging core 220 to the surface of the stent can be relatively easily calculated. In addition, as described above, because the stent is made of metal, an image of the vascular lumen surface on the rear surface of the stent cannot be obtained. However, a distance L1 to the vascular lumen surface when it is assumed that the stent is not present may be calculated by respectively coming into contact with both ends of the stent and setting an average value between two lines L' and L" where the stent is not detected to the distance L1.

$$L1=(L'+L'')/2$$

In addition, the cross-sectional image A-A' in FIG. 8 is displayed, a point which a user regards as the vascular lumen surface is indicated at multiple locations, and the multiple points are interpolated in a cubic spline. In this manner, the distance L1 may be obtained by generating a closed curve representing a virtual vascular lumen surface and referring to the generated closed curve.

For example, a thickness d of the stent is known depending on a type of the stent, and can be set in advance. Accordingly, a gap (in general, called a malapposition) MP between the rear surface of the stent 850 and the vascular lumen surface 801 can be obtained by using the following equation:

$$MP=L1-\{L0+d\}$$

For example, when the malapposition MP is greater than zero, an indication that "the malapposition is present" between the stent 850 and the vascular lumen surface 801 is shown. In order to allow some error, a predetermined non-negative threshold value $TH_{mp1}$ can be set in the embodiment. When a relationship satisfies $MP>TH_{mp1}$, it can be determined that the malapposition is present. A pixel for determining the presence or absence of the malapposition may be set to a pixel which is adjacent to a pixel determined to belong to the stent and is determined to belong to the vascular lumen surface.

In addition, a case of L1<L0 indicates a state where the stent is covered with the vascular tissues. However, a non-negative threshold value $TH_{mp2}$ is set in order to allow some errors. When a case where the relationship satisfies $L0-L1<TH_{mp2}$ indicates the state where the stent is covered with the vascular tissues. A determination-targeted pixel is set to be the same as that of the malapposition.

Next, distinction between the guidewire 250 and the stent 850 will be described. As previously described, the guidewire 250 can be made of metal similarly to the stent 850. Accordingly, luminance distribution of the line data in which the stent can be present resembles luminance distribution of the guidewire 250. The guidewire 250 is not always disposed by keeping a suitable distance from the inner surface of the stent 850, and may be disposed by being in contact with the inner surface of the stent 850. Accordingly, it can be difficult to distinguish the guidewire and the stent from each other on one cross-sectional image.

In accordance with an exemplary embodiment, the stent 850 can be caused to indwell only a treatment-targeted region and the pull-back processing can be performed by including an outside region of the treatment-targeted region in order to observe the entire treatment-targeted region. For example, the guidewire 250 can be detected throughout the pull-back region, and the stent appears in only a specified region where the pull-back processing is performed. By utilizing this characteristic, the guidewire and the stent can be distinguished from each other as follows.

First, a direction of an angle θ where the line data having a high luminance pixel detected is present is determined as a candidate point of the stent for a single tomographic image of an end portion in the pull-back processing. Then, the stent candidate is also similarly obtained for the adjacent tomographic image, and the candidate point having the angle closest to the candidate point on the adjacent tomographic image is detected, thereby performing grouping. This processing is performed for the other end portion of the pull-back processing, thereby calculating a group of one candidate point continuous throughout the entire region of the pull-back processing. The candidate point configuring one group is recognized as the guidewire 250.

The processing in the embodiment has been described. However, the outline is as follows.

Based on the line data obtained by the pull-back processing, the signal processing unit 428 builds each cross-sectional tomographic image along the z axis which serves as a three-dimensional tomographic image as usual, that is, builds three-dimensional volume data (refer to FIG. 5). Then, the signal processing unit 428 converts the luminance value in each line data in accordance with the opacity conversion curve f. In accordance with the previously described principle, the signal processing unit 428 calculates each pixel value P (z, θ) configuring the two-dimensional image which is fundamental to θ-z in the embodiment. At this time, discrimination processing of the stent and the guidewire is also performed. According to the processing until now, each pixel of the two-dimensional image is determined to belong to any one of the stent, the guidewire, and the vascular lumen surface.

Next, the signal processing unit 428 obtains the distance L0 between a pixel P1 which belongs to the stent and is adjacent to the pixel of the vascular lumen and the rotation center position on the tomographic image. In addition, the signal processing unit 428 obtains the distance L1 between a pixel P2 which belongs to the vascular lumen and is adjacent to the pixel P1 of the stent and the rotation center position on the tomographic image. Then, based on the preset thickness d of the stent, and the distances L0 and L1 the signal processing unit 428 determines whether or not the pixel P2 (or P1) configures the malapposition, or determines whether or not the stent is covered with the tissues of the vascular lumen, and adds correction to the determination result in order to perform emphasis processing of the pixel value P2. In an exemplary embodiment, as the correction processing, correction of the pixel value is added so as to become a line segment of a broken thick line, a solid line, and a broken normal line along the pixel P2.

Figure 9:
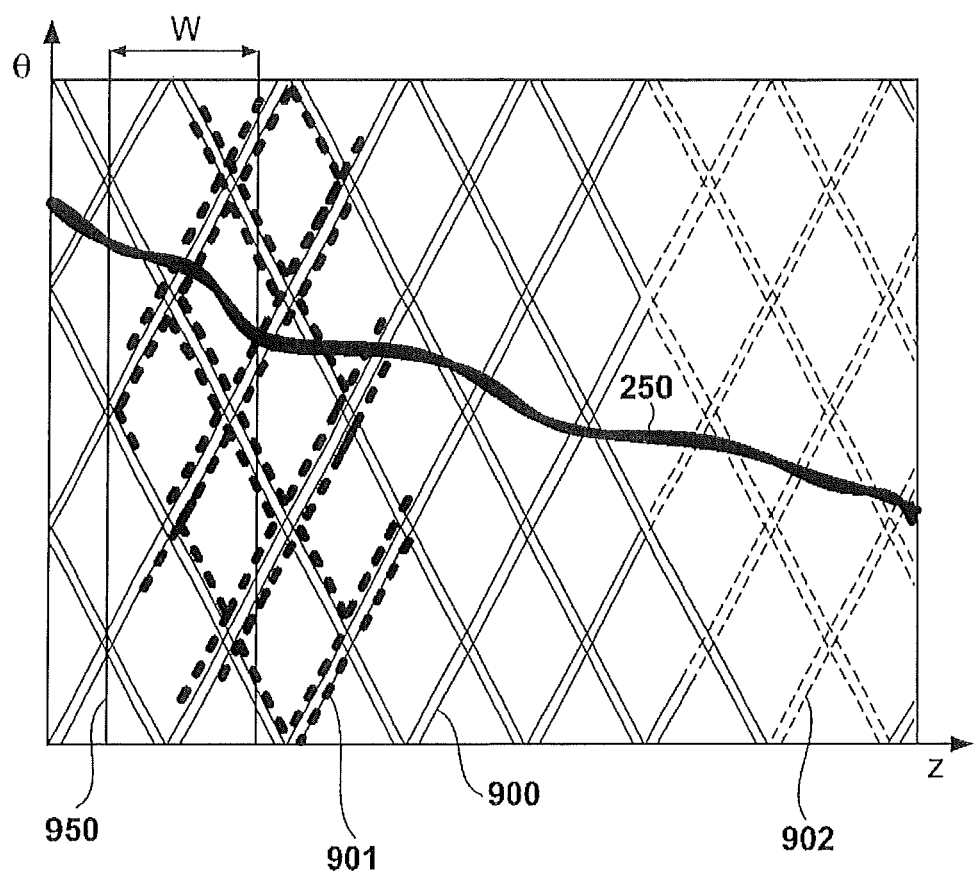
FIG. 9 is a view illustrating an example of the two-dimensional image generated for a progress examination of the stent according to an exemplary embodiment.

FIG. 9 illustrates an example of the two-dimensional image generated by adding the above-described correction processing. In FIG. 9, the vertical axis is θ, and the horizontal axis is the direction z (longitudinal direction of the blood vessel=pull-back direction). FIG. 9 illustrates the two-dimensional image of θ-z, and thus the image comes to have a rectangular shape.

The reference numeral 900 which forms the illustrated mesh represents an image of the stent. A broken thick line 901 indicates that the stent in which the thick broken line serves as a boundary line on both sides configures the malapposition (that a gap is present between the rear surface of the stent and the vascular lumen surface). In addition, a broken thin line 902 indicates that the stent is covered with the tissues of the vascular lumen at the portion. A curve 250 indicates the guidewire. However, as described above, the discrimination of the guidewire from the stent is performed. Thus, an edge of the curve 250 is not a display target for indicating the malapposition or that the stent is covered with the vascular lumen tissues.

According to the two-dimensional image in FIG. 9, a stabilized state where the malapposition is formed in an entire angular range on the left side of the stent can be understood, and where the entire angular region on the right side of the stent is covered with the vascular tissues.

Figure 10:
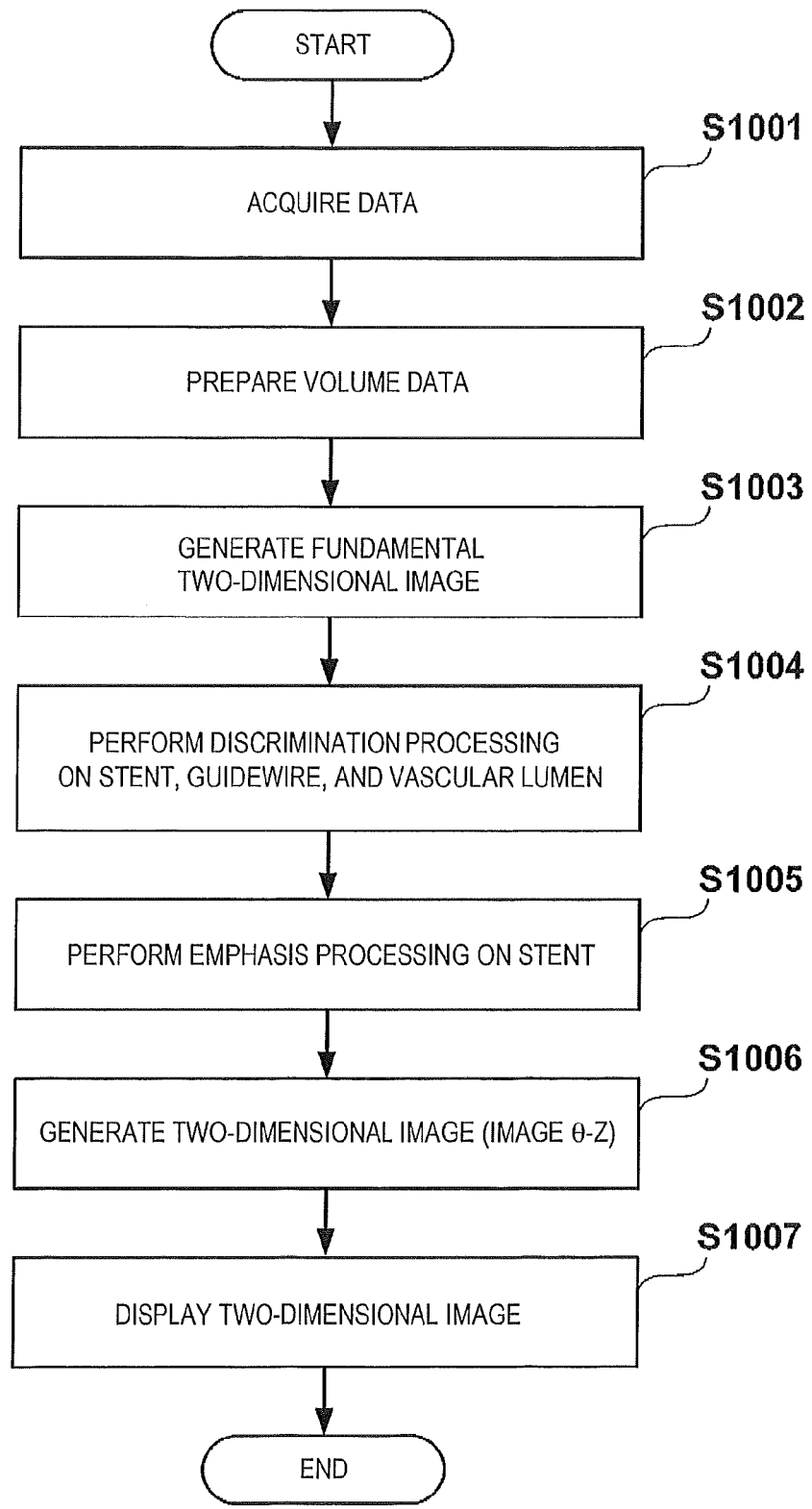
FIG. 10 is a flowchart illustrating a processing procedure according to an exemplary embodiment.

The signal processing unit 428 which has completed the pull-back processing may consequently generate each cross-sectional image according to the flowchart in FIG. 10. Hereinafter, processing of the signal processing unit 428 will be described with reference to the drawing. In practice, a processing procedure according to the flowchart in the drawing can be stored, for example, in a hard disk device or the like, as a program executed by the signal processing unit.

First, in Step S1001 line data acquired by the pull-back processing is received and stored in the memory 428*a*. Next, in Step S1002, the signal processing unit 429 reconfigures each cross-sectional image, and generates three-dimensional volume data (refer to FIG. 5). The generation processing is known, and thus description of the known generation process will be omitted here.

In subsequent Step S1003, the signal processing unit 428 calculates each pixel value P (z, θ) of the two-dimensional image which is fundamental. Thereafter, in Step S1004, the signal processing unit 428 performs processing for discriminating whether each pixel unit belongs to any one of the stent, the guidewire, and the vascular lumen. Although details have been described above, as an initial value, the signal processing unit 428 may determine all pixels belong to the vascular lumen. Thereafter, the signal processing unit 428 may determine that the pixel P having high reflectivity belongs to the guidewire and the stent.

In Step S1005, the signal processing unit 428 refers to the volume data, and determines whether or not the pixel adjacent to the stent among the pixels belonging to the vascular lumen configures the malapposition, or whether or not the stent is covered with the vascular tissues. Based on the determination result, the signal processing unit 428 performs emphasis processing so that both of these can be distinguished from each other. In FIG. 9, a pixel value is corrected so that the pixel belonging to the malapposition is illustrated by the broken thick line, the portion covered with the vascular tissues is illustrated by the broken line, and the others (state where the rear surface of the stent is in contact with the vascular lumen surface) are illustrated by the solid line. In Step S1006, the signal processing unit 428 generates the two-dimensional image for display together with various user interface components. Then, in Step S1007, the signal processing unit 428 displays the generated two-dimensional image of θ-z and the generated user interface components, on the LCD monitor 113.

Figure 11:
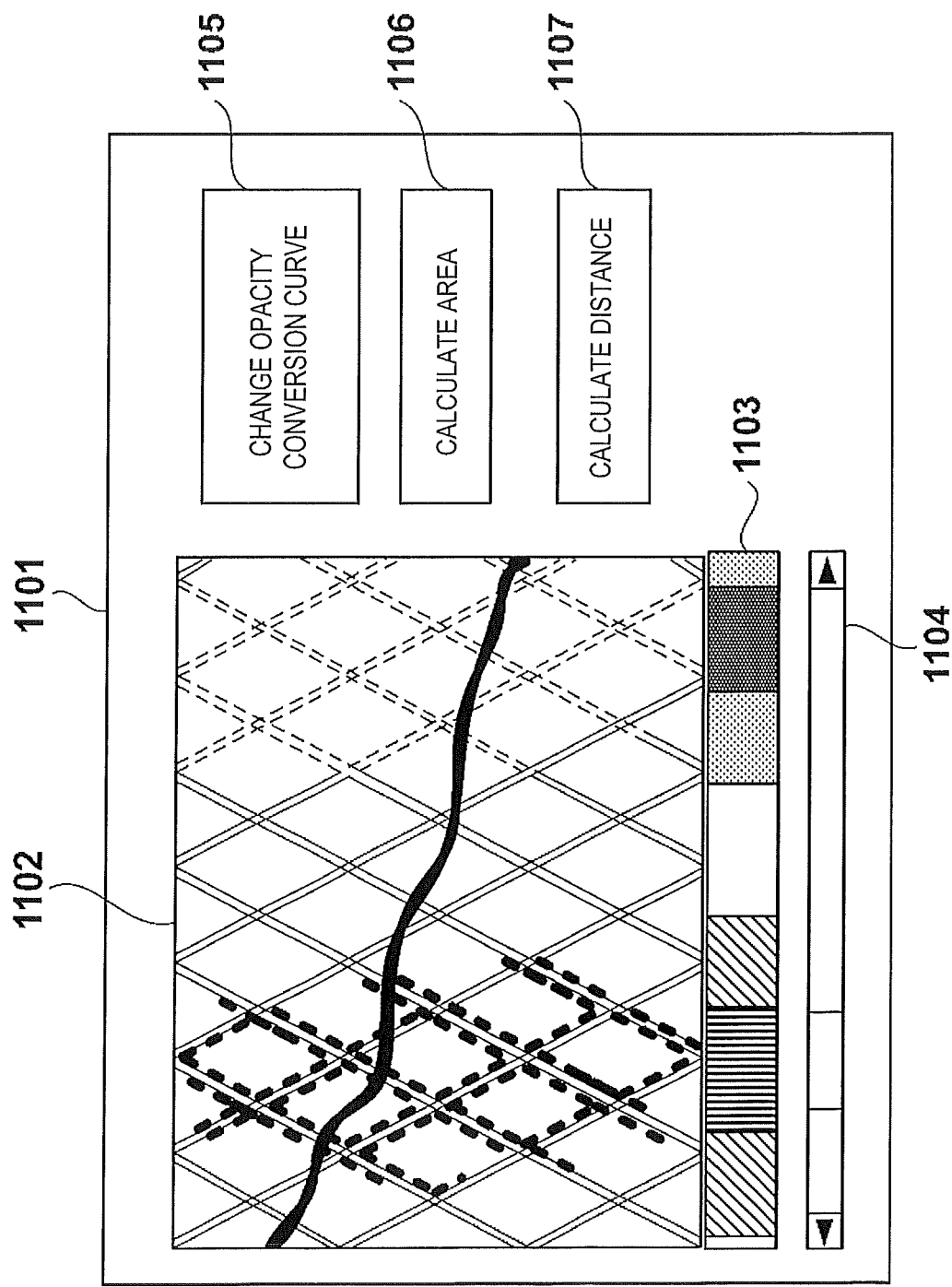
FIG. 11 is a view illustrating an example of a user interface displayed on a display screen of the imaging apparatus for diagnosis according to an exemplary embodiment.

Here, FIG. 11 illustrates an example of a user interface displayed on a screen of the LCD 113, and the example will be described as follows.

The reference numeral 1101 illustrated in the drawing represents a window displayed on the screen of the LCD 113. The window 1101 has a region 1102 for displaying the two-dimensional image of the space θ-z, a state region for visually displaying a degree of the malapposition along the z axis and a degree where the stent is covered with vascular tissues, a scroll bar 1104 for scrolling in the z axis direction (in order to deal with a case where the distance of the pull-back processing exceeds the width of the screen), a button 1105 for instructing a change in the opacity conversion curve, an area calculation button 1106, and a distance calculation button 1107.

The region 1103 displays an occurrence degree of the malapposition along the z axis direction on the two-dimensional image displayed in the region 1102 and the degree where the stent is covered with vascular tissues, and is disposed in order to display the degrees in a one-dimensional manner through multiple stages.

A degree D of the malapposition is calculated according to the following equation, for example, when as illustrated in FIG. 9, a horizontal direction is set to W, the number of all pixels within a rectangular region 950 defined in all angular regions in a vertical direction is set to N, the number of pixels determined to have the malapposition within the region is set to Nm, and a preset multiplication factor is set to α.

$$D=\alpha \cdot Nm/N$$

In addition, a ratio where the stent is covered with the vascular tissues may be calculated similarly.

If the opacity conversion curve 1105 is clicked by the mouse 114, the signal processing unit 428 displays a GUI (graphical user interface) for moving the conversion curve illustrated in FIG. 7 in parallel along the luminance axis in the horizontal direction, thereby enabling a user to freely change the position of the conversion curve. Then, the signal processing unit 428 recalculates and displays the two-dimensional image of θ-z in accordance with the changed conversion curve. For example, when the conversion curve 700 in FIG. 7 is moved in parallel to the right side, the opacity from the vascular lumen surface to a certain degree depth is set to amin. Accordingly, a deeper layer can be displayed as the vascular lumen surface.

The area calculation button 1106 is clicked or disposed in order to calculate an actual area of the vascular lumen surface when a user draws a closed curve within the illustrated region 1102. In the embodiment, the vertical axis is θ, which is different from an axis in the three-dimensional space visible to humans. Accordingly, even when the closed curve is drawn within the region 1102 by the mouse 114, it can be difficult to estimate the actual area of the vascular lumen surface, based on the drawn result. Therefore, in the embodiment, after the button 1106 is clicked, the signal processing unit 428 obtains an actual three-dimensional position by projecting each pixel value connecting line segments when the closed curve including any optional position in the region 1102 is drawn, to a three-dimensional model. This processing is performed for each pixel position so as to determine multiple pixel positions for defining the closed curve in the actual three-dimensional space. Thereafter, the signal processing unit 428 calculates the area, and displays the result on the screen.

The distance calculation button 1107 is clicked or disposed to display a distance in such a way that a user designates two desired points within the illustrated region 1102, the two points are projected to the three-dimensional model representing the actual vascular lumen surface, and the distance between the two projected points is calculated.

Hitherto, the embodiment has been described. However, the present disclosure is not limited to the above-described embodiment. For example, in the embodiment, the pixel value representing the vascular tissues is corrected so as to visually display the presence or absence of the malapposition, whether or not the stent is covered with the vascular tissues. However, a correction-targeted pixel may be a pixel belonging to the stent. In addition, without being limited to the broken thick line, the solid line, and broken thin line, display forms may be displayed by colors. In addition, for example, the malapposition may be displayed at multiple stage levels depending on the distance between the rear surface of the stent and the vascular lumen surface. In a case of the multiple stage display, a degree of the malapposition may be displayed by using a color density. The thickness when the stent is covered with the vascular tissues may also be displayed in this manner.

As is understood from the above-described embodiment, processing for the reconfiguration of the cross-sectional image and the two-dimensional reconfiguration are performed by the signal processing unit 428 configured to have a microprocessor. The microprocessor executes a program so as to realize a function thereof. Accordingly, the program is also included within the scope of the present disclosure, as a matter of course. In addition, the program is generally stored in a computer-readable storage medium such as a CD-ROM, a DVD-ROM, or the like. The computer-readable storage medium is set in a reading device (CD-ROM drive or the like) included in a computer. The program can be executed by being copied to or installed in a system. Therefore, it is apparent that the related computer-readable storage medium is also included within the scope of the present disclosure.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. An imaging apparatus for diagnosis which reconfigures a three-dimensional image of a blood vessel by using a probe emitting light toward a vascular lumen surface, and accommodating an imaging core for detecting reflection light from the blood vessel, and to move the imaging core along the probe at a predetermined speed while the imaging core is rotated, the apparatus comprising:
   a processor configured to:
      derive line data configured to include multiple luminance values arrayed side by side in a radial direction from a rotation center of the imaging core per each rotation angle in a rotation, based on data obtained by the imaging core during a period while the imaging core is rotated and moved; and
      calculate a two-dimensional image data in which θ, z are set to two axes, by calculating a representative pixel value P (θ, z) in a viewing direction toward the radial direction from the rotation center of the imaging core in each line data L (θ, z), where the rotation angle of the imaging core is defined as θ and the line data at a movement position z in the movement is defined as L (θ, z); and
   a display for displaying the calculated two-dimensional image data.

2. The imaging apparatus for diagnosis according to claim 1, wherein the processor is configured to:
   generate three-dimensional model data of the blood vessel, based on each line data obtained;

discriminate whether or not each line data obtained is line data indicating a stent indwelling the blood vessel;

specify a portion where a malapposition having a predetermined threshold value or greater is present between a vascular lumen surface and a surface of the stent opposing the vascular lumen surface, based on the discrimination result, the three-dimensional model data, and a preset thickness d of the stent;

calculate a representative pixel value of the line data by converting a luminance value of each line data into a value indicating opacity using a preset conversion function, and by continuously adding the value indicating the opacity of a luminance value along the radial direction from the center position of the rotation; and correct a pixel value corresponding to a portion specified within image data configured to have the representative pixel value, and for generating the two-dimensional image data for highlighting the portion where the malapposition is present.

3. The imaging apparatus for diagnosis according to claim 2, wherein the conversion function is a function which has a conversion curve in a shape of linearly connecting a minimum opacity in a case of two preset luminance values IL or smaller, a maximum opacity in a case of a luminance value IH greater than the luminance value IL or greater, and the minimum opacity and the maximum opacity between the luminance values IL and IH.

4. The imaging apparatus for diagnosis according to claim 3, wherein the processor is configured to:
move the conversion curve in parallel along the luminance axis in response to a user's instruction.

5. The imaging apparatus for diagnosis according to claim 2, wherein the processor is configured to:
specify a portion where the stent is covered with vascular tissues, and in which a relationship satisfies L0>L1 between a distance L0 between the imaging core and the surface of the stent and a distance L1 between the imaging core in the vicinity of a measurement position of the distance L0 and the vascular lumen surface, based on the discrimination result, and
correct a pixel of the portion where the stent is covered with the vascular tissues within the image data configured to have the representative pixel value.

6. The imaging apparatus for diagnosis according to claim 5, wherein the processor is configured to:
generate a guide image indicating a ratio of the malapposition present at each position in the z axis of the two-dimensional image, and a ratio of the stent covered with the vascular tissues, wherein
the display displays the two-dimensional image data and the guide image in parallel with each other along the z axis.

7. A control method of an imaging apparatus for diagnosis in which a three-dimensional image of a blood vessel is reconfigured by using a probe emitting light toward a vascular lumen surface and accommodating an imaging core for detecting reflection light from the blood vessel, and to move the imaging core along the probe at a predetermined speed while the imaging core is rotated, the method comprising:
deriving line data configured to include multiple luminance values arrayed side by side in a radial direction from a rotation center of the imaging core per each rotation angle in a rotation, based on data obtained by the imaging core during a period while the imaging core is rotated and moved;

calculating two-dimensional image data in which $\theta$, z are set to two axes, by calculating a representative pixel value $P(\theta, z)$ in a viewing direction toward the radial direction from the rotation center of the imaging core in each line data $L(\theta, z)$, where the rotation angle of the imaging core is defined as $\theta$ and the line data at a movement position z in the movement is defined as $L(\theta, z)$; and displaying the calculated two-dimensional image data.

8. The method according to claim 7, wherein the calculating two-dimension image date includes:
generating three-dimensional model data of the blood vessel, based on each line data;
discriminating whether or not each line data is line data indicating a stent indwelling the blood vessel;
specifying a portion where a malapposition having a predetermined threshold value or greater is present between a vascular lumen surface and a surface of the stent opposing the vascular lumen surface, based on the discrimination result, the three-dimensional model data, and a preset thickness d of the stent;
calculating a representative pixel value of the line data by converting a luminance value of each line data into a value indicating opacity using a preset conversion function, and by continuously adding the value indicating the opacity of a luminance value along the radial direction from the center position of the rotation; and
correcting a pixel value corresponding to a portion within image data configured to have the representative pixel value, and for generating the two-dimensional image data for highlighting the portion where the malapposition is present.

9. The method according to claim 8, wherein the conversion function is a function which has a conversion curve in a shape of linearly connecting a minimum opacity in a case of two preset luminance values IL or smaller, a maximum opacity in a case of a luminance value IH greater than the luminance value IL or greater, and the minimum opacity and the maximum opacity between the luminance values IL and IH.

10. The method according to claim 9, comprising:
moving the conversion curve in parallel along the luminance axis in response to a user's instruction.

11. The method according to claim 8, comprising:
specifying a portion where the stent is covered with vascular tissues, and in which a relationship satisfies L0>L1 between a distance L0 between the imaging core and the surface of the stent and a distance L1 between the imaging core in the vicinity of a measurement position of the distance L0 and the vascular lumen surface, based on the discrimination result, and
correcting a pixel of the portion where the stent is covered with the vascular tissues within the image data configured to have the representative pixel value.

12. The method according to claim 11, comprising:
generating a guide image indicating a ratio of the malapposition present at each position in the z axis of the two-dimensional image, and a ratio of the stent covered with the vascular tissues; and
displaying the two-dimensional image data and the guide image in parallel with each other along the z axis.

13. An information processing apparatus that generates a three-dimensional image, based on data transmitted from an imaging core obtained from an imaging apparatus for diagnosis which reconfigures the three-dimensional image of a blood vessel by using a probe emitting light toward a vascular lumen surface and accommodating an imaging core for detecting reflection light from the blood vessel, and to move the imaging core along the probe at a predetermined speed while the imaging core is rotated, the information processing apparatus comprising:
- a processor configured to:
  - derive line data configured to include multiple luminance values arrayed side by side in a radial direction from a rotation center of the imaging core per each rotation angle in a rotation, based on data obtained by the imaging core during a period while the imaging core is rotated and moved;
- calculate two-dimensional image data in which θ, z are set to two axes, by calculating a representative pixel value P (θ, z) in a viewing direction toward the radial direction from the rotation center of the imaging core in each line data L (θ, z), when the rotation angle of the imaging core is defined as θ and the line data at a movement position z in the movement is defined as L (θ, z); and
- a display for displaying the calculated two-dimensional image data.

14. A control method of an information processing apparatus that generates a three-dimensional image, based on data transmitted from an imaging core obtained from an imaging apparatus for diagnosis which reconfigures the three-dimensional image of a blood vessel by using a probe emitting light toward a vascular lumen surface and accommodating an imaging core for detecting reflection light from the blood vessel, and to move the imaging core along the probe at a predetermined speed while the imaging core is rotated, the method comprising:
- deriving line data configured to include multiple luminance values arrayed side by side in a radial direction from a rotation center of the imaging core per each rotation angle in a rotation, based on data obtained by the imaging core during a period while the imaging core is rotated and moved;
- calculating two-dimensional image data in which θ, z are set to two axes, by calculating a representative pixel value P (θ, z) in a viewing direction toward the radial direction from the rotation center of the imaging core in each line data L (θ, z), when the rotation angle of the imaging core is defined as θ and the line data at a movement position z in the movement is defined as L (θ, z); and
- displaying the calculated two-dimensional image data.

15. A program that is read by a computer and causes the computer to execute the method according to claim 14.

16. A non-transitory computer-readable recording medium with a program stored therein which causes a computer to execute a control method of an information processing apparatus that generates a three-dimensional image, based on data transmitted from an imaging core obtained from an imaging apparatus for diagnosis which reconfigures the three-dimensional image of a blood vessel by using a probe emitting light toward a vascular lumen surface and accommodating an imaging core for detecting reflection light from the blood vessel, and to move the imaging core along the probe at a predetermined speed while the imaging core is rotated, the method comprising:
- deriving line data configured to include multiple luminance values arrayed side by side in a radial direction from a rotation center of the imaging core per each rotation angle in a rotation, based on data obtained by the imaging core during a period while the imaging core is rotated and moved;
- calculating two-dimensional image data in which θ, z are set to two axes, by calculating a representative pixel value P (θ, z) in a viewing direction toward the radial direction from the rotation center of the imaging core in each line data L (θ, z), when the rotation angle of the imaging core is defined as θ and the line data at a movement position z in the movement is defined as L (θ, z); and
- displaying the calculated two-dimensional image data.

* * * * *